United States Patent
Johnson et al.

(10) Patent No.: US 8,940,924 B2
(45) Date of Patent: Jan. 27, 2015

(54) MIXED OXIDE CATALYST AND A PROCESS FOR THE PRODUCTION OF ETHYLENICALLY UNSATURATED CARBOXYLIC ACIDS OR ESTERS

(75) Inventors: David William Johnson, Wilton (GB); Sabina Ziemian, Wilton (GB)

(73) Assignee: Lucite International UK Limited, Southampton (GB)

(*) Notice: Subject to any disclaimer, the term of this patent is extended or adjusted under 35 U.S.C. 154(b) by 0 days.

(21) Appl. No.: 13/805,052

(22) PCT Filed: Jun. 24, 2011

(86) PCT No.: PCT/GB2011/051194
§ 371 (c)(1),
(2), (4) Date: Mar. 1, 2013

(87) PCT Pub. No.: WO2012/001394
PCT Pub. Date: Jan. 5, 2012

(65) Prior Publication Data
US 2013/0178647 A1 Jul. 11, 2013

(30) Foreign Application Priority Data
Jul. 1, 2010 (GB) .................................. 1011091.4

(51) Int. Cl.
| | | |
|---|---|---|
| C07C 67/30 | (2006.01) | |
| C07C 51/347 | (2006.01) | |
| B01J 23/10 | (2006.01) | |
| B01J 23/08 | (2006.01) | |
| B01J 23/16 | (2006.01) | |
| B01J 23/20 | (2006.01) | |
| B01J 23/14 | (2006.01) | |
| B01J 23/00 | (2006.01) | |
| B01J 23/18 | (2006.01) | |
| B01J 37/03 | (2006.01) | |
| C07C 51/353 | (2006.01) | |
| C07C 67/343 | (2006.01) | |

(52) U.S. Cl.
CPC ............... B01J 23/20 (2013.01); B01J 23/002 (2013.01); B01J 23/08 (2013.01); B01J 23/10 (2013.01); B01J 23/18 (2013.01); B01J 37/031 (2013.01); C07C 51/353 (2013.01); C07C 67/343 (2013.01); C07C 51/347 (2013.01); C07C 67/30 (2013.01); B01J 2523/00 (2013.01)
USPC ........... 560/211; 562/599; 502/302; 502/303; 502/349; 502/350; 502/354

(58) Field of Classification Search
None
See application file for complete search history.

(56) References Cited

U.S. PATENT DOCUMENTS

| | | |
|---|---|---|
| 3,865,873 A | 2/1975 | Oda et al. |
| 5,808,148 A | 9/1998 | Gogate et al. |
| 5,998,657 A | 12/1999 | Gogate et al. |
| 6,043,185 A | 3/2000 | Cirjak et al. |
| 6,084,135 A | 7/2000 | Wachs |
| 6,252,122 B1 * | 6/2001 | Tenten et al. .................. 568/475 |
| 6,683,221 B1 | 1/2004 | Wachs |
| 7,304,014 B2 | 12/2007 | Cavalcanti et al. |
| 2003/0009058 A1 | 1/2003 | Canos et al. |

FOREIGN PATENT DOCUMENTS

| | | |
|---|---|---|
| EP | 0 111 605 A1 | 6/1984 |
| EP | 0111605 A1 | 6/1984 |
| EP | 1243574 A1 | 9/2002 |
| EP | 1 574 255 A2 | 9/2005 |
| EP | 1574255 A2 | 9/2005 |
| JP | 2 966650 B2 | 10/1999 |
| JP | 2966650 B2 | 10/1999 |
| JP | 2005213182 A | 8/2005 |
| WO | 9933778 A1 | 7/1999 |
| WO | 0056692 A1 | 9/2000 |

OTHER PUBLICATIONS

Russian Office Action for Russian Application No. 2013104203/20(006159) dated Jan. 31, 2013.
UK Search Report for Application No. GB1011091.4 dated Apr. 15, 2011.
International Preliminary Report on Patentability from the International Bureau for International Application No. PCT/GB2011/051194 dated Jan. 17, 2013.
International Search Report and Written Opinion of the International Searching Authority for International Application No. PCT/GB2011/051194 dated Oct. 10, 2011.
International Search Report for PCT/GB2011/051194 dated Oct. 10, 2011.

* cited by examiner

*Primary Examiner* — Jafar Parsa
*Assistant Examiner* — Amy C Bonaparte
(74) *Attorney, Agent, or Firm* — Shumaker, Loop & Kendrick, LLP

(57) ABSTRACT

The invention relates to a catalyst for the reaction of formaldehyde with a carboxylic acid or ester to produce an ethylenically unsaturated carboxylic acid or ester, preferably α, β ethylenically unsaturated carboxylic acids or ester. The catalyst includes a metal oxide having at least two types of metal cations, $M^1$ and $M^2$, wherein $M^1$ is at least one metal selected from group 3 or 4 in the $4^{th}$ to $6^{th}$ periods of the periodic table, group 13 in the $3^{rd}$ to $5^{th}$ periods of the periodic table, or the remaining elements in the lanthanide series and $M^2$ is at least one metal selected from group 5 in the $5^{th}$ or $6^{th}$ periods of the periodic table or group 15 in the $4^{th}$ or $5^{th}$ periods of the periodic table. The production includes reacting formaldehyde with a carboxylic acid or ester in the presence of the catalyst effective to catalyze the reaction.

16 Claims, No Drawings

MIXED OXIDE CATALYST AND A PROCESS FOR THE PRODUCTION OF ETHYLENICALLY UNSATURATED CARBOXYLIC ACIDS OR ESTERS

RELATED APPLICATIONS

This application is a US National Stage Application that claims the benefit of prior filed, co-pending, PCT application number PCT/GB2011/051194 filed on Jun. 24, 2011. Both this application and the aforementioned PCT application also claim priority from GB Application 1011091.4 filed on Jul. 1, 2010. Both the PCT Application and the GB Application are herein incorporated by reference.

TECHNICAL FIELD AND BACKGROUND OF THE INVENTION

The present invention relates to mixed oxide catalysts and a process for the production of ethylenically unsaturated carboxylic acids or esters, particularly α, β unsaturated carboxylic acids or esters, more particularly (alk)acrylic acids or alkyl (alk)acrylates such as (meth)acrylic acid or alkyl (meth)acrylates by the condensation of carboxylic acid or esters with formaldehyde or a source thereof in the presence of mixed oxide catalysts, in particular, but not exclusively, a process for the production of (meth) acrylic acid or alkyl esters thereof, for example, methyl methacrylate, by the condensation of propionic acid or alkyl esters thereof with formaldehyde or a source thereof in the presence of such mixed oxide catalysts.

SUMMARY OF THE INVENTION

Such acids or esters may be made by reacting an alkanoic acid (or ester) of the formula $R^3$—$CH_2$—$COOR^4$, where $R^3$ and $R^4$ are each, independently, a suitable substituent known in the art of acrylic compounds such as hydrogen or an alkyl group, especially a lower alkyl group containing, for example, 1-4 carbon atoms, with a suitable methylene source, for example, a source of formaldehyde. Thus, for instance, methacrylic acid or alkyl esters thereof, especially methyl methacrylate, may be made by the catalytic reaction of propionic acid, or the corresponding alkyl ester, e.g. methyl propionate, with formaldehyde as a methylene source in accordance with the reaction sequence 1.

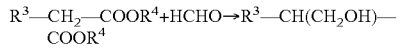

and

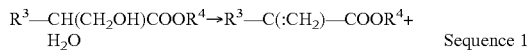  Sequence 1

An example of reaction sequence 1 is reaction sequence 2

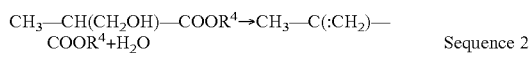  Sequence 2

The above reaction Sequence 1 or 2 is typically effected at an elevated temperature, usually in the range 250-400° C., using an acid-base catalyst. Where the desired product is an ester, the reaction is preferably effected in the presence of the relevant alcohol in order to minimise the formation of the corresponding acid through hydrolysis of the ester. Also for convenience it is often desirable to introduce the formaldehyde in the form of formalin. Hence, for the production of methyl methacrylate, the reaction mixture fed to the catalyst will generally consist of methyl propionate, methanol, formaldehyde and water.

Conventionally, methyl methacrylate has been produced industrially via the so-called acetone-cyanohydrin route. The process is capital intensive and produces methyl methacrylate at a relatively high cost.

U.S. Pat. No. 4,560,790 describes the production of α, β unsaturated carboxylic acids and esters by the condensation of methylal with a carboxylic acid or ester using a catalyst of general formula $M^1/M^2/P/O$ wherein $M^1$ is a group IIIb metal, preferably aluminium, and $M^2$ is a group IVb metal, preferably silicon.

Sumitomo (JP2005213182) have disclosed metal oxynitride catalysts for the preparation of α,β-unsaturated products using formaldehyde, nitriding single metal oxides such as $Ta_2O_5$ by thermal treatment with ammonia. The resultant oxynitrides catalysed the gas-phase condensation of formaldehyde (trioxane source) with propionic acid to methacrylic acid. Sumitomo also disclose the possibility of putting these single metal oxides on a support such as silica or alumina.

EP 1 243 574 discloses the use of Aluminium phosphates, silicoaluminophosphates and mesoporous amorphous alumina-silica and their nitrided or oxynitrided equivalents to catalyse the aldol condensation of an alkylaldehyde and benzaldehyde to α-n-amylcinnamaldehyde.

U.S. Pat. No. 5,998,657 discloses the use of niobium oxide as a catalyst in the reaction of alkyl esters or their acids with methanol and oxygen to produce the α,β-unsaturated ester or carboxylic acid product. Silica is used as a support for the niobium oxide.

As mentioned above, a known production method for MMA is the catalytic conversion of methyl propionate (MEP) to MMA using formaldehyde. A suitable catalyst for this is a caesium catalyst on a support, for instance, silica.

It has now been found that a particular combination of metal oxidation states and metal ionic sizes in a mixed metal oxide compound can provide a surprisingly high catalytic activity in the reaction of formaldehyde or a suitable source thereof with a carboxylic acid or ester to produce ethylenically unsaturated carboxylic acids or esters, particularly α, β ethylenically unsaturated carboxylic acids or esters.

According to a first aspect of the present invention there is provided a catalyst for the reaction of formaldehyde or a suitable source thereof with a carboxylic acid or ester to produce an ethylenically unsaturated carboxylic acid or ester, preferably α, β ethylenically unsaturated carboxylic acids or ester, wherein the catalyst comprises a metal oxide having at least two types of metal cations, $M^1$ and $M^2$, wherein $M^1$ is at least one metal selected from group 3 or 4 in the 4th to $6^{th}$ periods of the periodic table, group 13 in the $3^{rd}$ to $5^{th}$ periods of the periodic table, or the remaining elements in the lanthanide series (namely, scandium, yttrium, the lanthanide elements, titanium, zirconium, hafnium; aluminium, gallium, indium) and $M^2$ is at least one metal selected from group 5 in the $5^{th}$ or $6^{th}$ periods of the periodic table or group 15 in the $4^{th}$ or $5^{th}$ periods of the periodic table (namely, niobium, tantalum, arsenic and antimony).

It will be appreciated by the skilled person that the invention is distinct from the existence of an incidental monolayer of a single metal oxide catalyst formed on a support of another metal oxide. However, for the avoidance of doubt, typically, the catalyst cations, $M^1$ and $M^2$, and oxide anions are uniformly distributed throughout the metal oxide catalyst which catalyst extends to multiple molecular layers, more typically, at least 0.5 nm, most typically, at least 1 nm, especially, at least 2 nm average thickness. This would not be the case with a single metal oxide layer on a support where the metal of the support only interacts at the level of the catalyst monolayer on the support (typically, less than 0.5 nm thick) and not throughout the catalyst. Furthermore, in the invention, the metal cations, $M^1$ and $M^2$ and the oxide of the catalyst are exclusively from the catalyst and not from a support for the catalyst. Thus, in general, the catalyst of the invention is not a monolayer on a support for the catalyst but a multi-layered catalyst having the properties defined above in the first aspect of the invention throughout its substance.

Thus, in general, any of the cations or anions forming the metal oxide catalyst are not simultaneously metal cations or anions of a catalytic support unless, independent of the support, the catalyst is in accordance with the invention throughout its substance.

Typically, the metal oxide of the present invention exists and is used independently of any catalytic support. However, when used on a support, the mixed metal oxide provides a metal oxide catalytic surface having $M^1$ type and $M^2$ type cations and oxygen anions independently of any metal cations and oxygen anions forming or contributed by the support.

For the avoidance of doubt, by the lanthanide elements or series herein is meant La, Ce, Pr, Nd, Pm, Sm, Eu, Gd, Tb, Dy, Ho, Er, Tm, Yb, and Lu.

According to a second aspect of the present invention there is provided a process to produce an ethylenically unsaturated carboxylic acid or ester, preferably α, β ethylenically unsaturated carboxylic acids or ester, comprising the steps of reacting formaldehyde or a suitable source thereof with a carboxylic acid or ester, optionally in the presence of an alcohol, in the presence of a catalyst effective to catalyse the reaction wherein the catalyst comprises a metal oxide having at least two types of metal cations, $M^1$ and $M^2$, wherein $M^1$ is at least one metal selected from group 3 or 4 in the 4th to $6^{th}$ periods of the periodic table, group 13 in the $3^{rd}$ to $5^{th}$ periods of the periodic table, or the remaining elements in the lanthanide series (namely, scandium, yttrium, the lanthanide elements, titanium, zirconium, hafnium; aluminium, gallium, indium) and $M^2$ is at least one metal selected from group 5 in the $5^{th}$ or $6^{th}$ periods of the periodic table or group 15 in the $4^{th}$ or $5^{th}$ periods of the periodic table (namely, niobium, tantalum, arsenic and antimony).

Advantageously, use of the catalyst of the present invention has been found to produce remarkably low levels of unwanted side products in the reaction of formaldehyde or a suitable source thereof with a carboxylic acid or ester to produce an ethylenically unsaturated carboxylic acid or ester. In particular, remarkably low levels of dimethyl ether (DME) and toluene are produced compared to conventional catalysts such as aluminium phosphate. In addition, the catalysts provide excellent selectivity and activity.

Preferably, $M^1$ is selected from the groups 3 or 4 in the $4^{th}$-$6^{th}$ periods of the periodic table. Optionally, $M^1$ may be selected from scandium, the lanthanide elements, titanium, zirconium, hafnium; gallium, indium or more likely scandium, the lanthanide elements, titanium, zirconium and hafnium such as scandium, lanthanum, titanium, zirconium and hafnium.

Preferably, $M^1$ are cations, preferably, in the 3+ oxidation state. Preferably, $M^2$ are cations, preferably, in the +5 oxidation state.

The said metal cations of the type $M^1$ and $M^2$, whether one or more of each type is present, may form from 40 to 100 mol % of the total metal present such as from 45, 47, 50, 55, 57, 60, 65 or 67 mol % in the metal oxide of the invention, more preferably, 70-100 mol % of the total metal present such as from 75 or 77 mol % in the metal oxide, most preferably, 80-100 mol % of the total metal present, especially, 90-100 mol % of the total metal present in the mixed metal oxide, more especially, 95-100 mol %, most especially, 97-100 mol %, particularly, substantially 100 mol %. If another metal of the type $M^3$ and/or $M^4$ set out below or another metal type is present, the metals of the type $M^1$ and $M^2$ may form up to 99.99 or 99.98 or 99.89 or 99.88 mol % of the total metal present, more typically, up to 99.90 or 99.80 or 99.70 mol % of the total metal present in the metal oxide with the same lower limits as already set out above.

Preferably, oxygen may form from 50 to 100 mol % of the total non-metal present in the metal oxide of the invention, more preferably, 70-100 mol % of the total non-metal present in the metal oxide, most preferably, 80-100 mol % of the total non-metal present, especially, 90-100 mol % of the total non-metal present in the metal oxide, more especially, 99%-100 mol %, most especially, substantially 100 mol %.

For the avoidance of doubt, non-metals herein does not include the "metalloid" elements boron, silicon, germanium, arsenic, antimony, tellurium and polonium but includes all elements having higher atomic numbers than the named element(s) in their respective period of the periodic table.

Preferably, the metal oxide forms 50-100 wt % of the catalyst, more preferably, 80-100 wt %, most preferably, 90-100 wt %, especially, 95-100 wt %, more especially, 97-100 wt %, most especially, 99-100 wt % of the catalyst. The balance of the catalyst is made up of impurities, binders or inert materials. Generally, the metal oxide forms about 100% of the catalyst.

However, when a binder is used in the present invention it may form up to 50 wt % of the catalyst. Alternatively, the binder may be used in conjunction with a catalyst support to bind the catalyst to the support. In the latter case, the binder does not form part of the catalyst as such.

Suitable binders for the catalyst of the present invention will be known to those skilled in the art. Non-limiting examples of suitable binders include silica (including colloidal silica), silica-alumina, such as conventional silica-alumina, silica-coated alumina and alumina-coated silica, and alumina, such as (pseudo)boehmite, gibbsite, titania, titania-coated alumina, zirconia, cationic clays or anionic clays such as saponite, bentonite, kaolin, sepiolite or hydrotalcite or mixtures thereof. Preferred binders are silica, alumina and zirconia or mixtures thereof.

The metal oxide particles can be embedded in the binder or vice versa. Generally, when used as part of the catalyst, the binder functions as an adhesive to hold the particles together. Preferably, the particles are homogeneously distributed within the binder or vice versa. The presence of the binder generally leads to an increase in mechanical strength of the final catalyst.

The typical average surface area of the metal oxide catalyst is in the range 2-1000 $m^2 g^{-1}$, more preferably, 5-400 $m^2 g^{-1}$, most preferably, 10-300 $m^2 g^{-1}$ as measured by the B.E.T. multipoint method using a Micromeritics TriStar 3000 Surface Area and porosity Analyser. The reference material used for checking the instrument performance is a carbon black powder supplied by Micromeritics with a surface area of 30.6 $m^2/g$ (+/−0.75 $m^2/g$), part number 004-16833-00.

The typical average particle size of the catalyst particles is in the range 2 nm-10000 nm (10μ), more preferably, 5 nm-4000 nm (4μ), most preferably, 10 nm-3000 nm (3μ) as measured by a Malvern Zetasizer Nano S using dynamic light scattering and using NIST standards.

If the material is porous, it is preferably mesoporous with an average pore size of between 2 and 50 nm. Pore size can be determined by mercury intrusion porosimetry using NIST standards.

The average pore volume of the catalyst particles may be less than 0.01 cm$^3$/g but is generally in the range 0.01-2 cm$^3$/g as measured by nitrogen adsorption. However, microporous catalysts are not the most preferred because they may inhibit movement of reagents through the catalyst and a more preferred average pore volume is between 0.3-1.2 cm$^3$/g as measured by BET multipoint method using nitrogen adsorption according to ISO 15901-2:2006. The Micromeritics TriStar Surface Area and Porosity Analyser is used to determine pore volume as in the case of surface area measurements and the same standards are employed.

In the case of a non supported catalyst, the metal oxide may be used directly in the form of a catalyst particles either free flowing or together with a suitable binder to create a solid of the desired shape and/or size. The particles may be of any suitable size and therefore also in the form of powder, granules or beads either with or without binder. Typically, the catalyst is used in the form of a fixed bed and for this purpose may be used alone or on a support and in the latter case may include a suitable catalytic binder to bind it to the support.

However, it is also possible for the catalyst to be used on a support. In this case, the metal oxide catalyst may form a suitable surface coating on a suitable support for a catalyst.

For the purposes of the present invention, the support does not form part of the catalyst.

Preferred combinations of metal oxides for use in the present invention may be selected from the list consisting of:—Al\Sb oxide; Ti\Sb oxide; Ga\Sb oxide; In\Sb oxide; Al\Nb oxide; Zr\Nb oxide; Ga\Nb oxide; Y\Nb oxide; La\Nb oxide; Al\Ta oxide; La\Ta oxide; and Al\Sb\Nb oxide. The oxides are either unsupported or supported on a suitable support, for example, alumina, silica, silicon nitride, colloidal silica, titania or aluminium phosphate.

It will be understood by the skilled person that a catalyst of the invention may be added to a support by any suitable means. The catalyst may be fixed, preferably by calcination, onto a suitable support after deposition of the compound onto the support using a suitable salt in a suitable solvent and subsequent drying of the surface coated support. Alternatively, the catalyst or suitable catalyst salt precursors may be co-precipitated with the support or suitable support precursors such as a silica sol from a suitable solvent. Preferably, an oxide support is used, more preferably, an oxide support as mentioned herein.

It is also possible to use the catalyst of the present invention in a mixture or admixture with another catalyst according to the present invention or otherwise with or without a suitable binder.

The total level of mixed oxides, cations and anions and binder may be the same as set out herein.

However, a distinction should be drawn between a metal compound according to the invention and a monolayer of a metal compound on a metal oxide support where one or more components, metal $M^1/M^2$ and/or oxygen is provided by the surface compound and the other components, metal $M^2/M^1$ and/or oxygen is provided by the support. Such a monolayer arrangement is not a catalyst according to the present invention but rather a different catalyst which is supported. In this arrangement, the elements $M^1$, $M^2$ and O do not form a catalyst according to the invention throughout the catalyst material. The surface coating will consist of multiple layers and the layers other than the monolayer will not conform with the invention.

As mentioned above, although at least one metal of the type $M^1$ and one metal of the type $M^2$ are present in the catalyst, further metals or metal cations of the type $M^3$ and/or $M^4$ may also be present in the mixed metal oxide. Typically, when present, the at least one metal $M^3$ whether in the form of a cation or otherwise may form between 0.01 and 10 mol % of the total metal present, more preferably, 0.01-5 mol % of the total metal present, most preferably, 0.1-3 mol % of the total metal present in the metal oxide. Suitable $M^3$ metals include metals from groups 1 and 2 of the periodic table, more preferably, group 1, especially, lithium, sodium, potassium, rubidium and/or caesium.

Typically, when present, the at least one metal $M^4$ whether in the form of a cation or otherwise may form between 0.01 and 50 mol % of the total metal present, more preferably, 0.01-40 mol % of the total metal present, most preferably, 0.1-30 mol % of the total metal present in the metal oxide, especially, 0.1-20 mol %. Suitable $M^4$ metals include metals from group 14 of the periodic table, more preferably, silicon, germanium, tin and lead, most preferably, silicon. Preferably, no other metal types are present in the metal oxide catalyst compound of the present invention above a level of 0.1 mol % other than the types $M^1$, $M^2$ and optionally $M^3$ and/or $M^4$ as all defined herein, more typically, no other metal types are present in the metal oxide catalyst compound of the present invention above a trace level than the types $M^1$, $M^2$ and optionally $M^3$ and/or $M^4$ as all defined herein.

The metal $M^4$ is preferably chosen because it forms a tetrahedral structure with the oxygen anion in the mixed oxide catalyst. Typically, the $M^4$ metal forms a 4+ cation. It has been found that such $M^4$ metal cations generally do not affect the acid-base properties of the catalyst. Such cations tend to form glassy phases in the catalyst matrix.

Typically, it is possible to include two or more metals of the type $M^1$ and/or $M^2$ within the scope of the present invention, more typically, up to three metals of each type $M^1$ and/or $M^2$, most typically, up to two metals of each type $M^1$ and/or $M^2$, especially, up to two metals of one type and only one metal of the other type, more especially, only one metal of each type $M^1$ and $M^2$: all the above being possible with or without any one or more metal of the type $M^3$ and/or $M^4$.

Preferably, including the at least one $M^1$ and $M^2$ metal, the metal oxide compound may have up to four or more preferably up to three metal cations in total, most preferably, however, there are only two metal cations in the metal oxide. Therefore, it is especially preferred that the metal oxide compound consists of one or two each, more especially, one each of the metal cations $M^1$ and $M^2$ together with oxygen anions.

A further preferred formula for the metal oxide is therefore $M^1_n M^2_m M^3_q M^4_r O_p$ wherein $M^1$ is a cation, preferably, a 3+ cation and $M^2$ is a cation, preferably, a 5+ cation, n, m and p may be a positive integer or decimal number and q and r may be a positive integer or decimal number or zero. Generally, n and m may independently be between 0.1 and 20, more preferably, between 0.1 and 10, most preferably, between 0.1 and 5 whereas p is chosen to balance the positive charge provided by n and m. Generally, q and r may be between 0 and 20, more preferably, 0.1 and 10, most preferably, 0.1 and 5. In a particularly preferred formula n and m are both 1 and p is 4. For the avoidance of doubt, the values on n, m, r and q defined above are the total number for $M^1$, $M^2$, $M^3$ and $M^4$ type metals if more than one cation of each type is present.

Generally, the metal oxide of the present invention is a neutral molecule and therefore the negatively charged oxygen anions and optionally, any other non-metals balance the positively charged metals present.

As mentioned herein, the term metal oxide should be understood in the general chemical sense as an ionic or covalent compound having the general formula $(M^1)_n(M^2)_m(M^3)_q(M^4)_rO_p$ wherein n and m must be greater than 0 and can take a decimal value and q and r are independently greater than or equal to 0 and can also take a decimal value. Generally, a mainly ionic compound is formed by the metal oxides of the present invention. The metal oxide compound itself of the present invention should not be understood in any non-conventional sense as relating to an admixture of metals and/or oxides which do not form new oxide compounds as defined herein.

The mole ratio of $M^1$ to $M^2$ is generally in the range 10:1 to 1:10, more preferably, 5:1 to 1:5, most preferably, 3:1 to 1:3. It will be appreciated that oxygen will generally be present at a level to balance the total cationic charge.

Typically, $M^1$ may be selected from one or more of the metals in the list consisting of: Scandium, yttrium, the lanthanide elements, titanium, hafnium, aluminium, gallium or indium, more preferably, Al(3+), Ga(3+), Y(3+), In(3+) or La(3+), most preferably, Ga(3+), Y(3+), In(3+), or La(3+), especially, La(3+) or Ga(3+).

Typically, $M^2$ may be selected from one or more metals in the list consisting of Nb(5+), Sb(5+) or Ta(5+), more preferably, Nb(5+) or Sb(5+), most preferably, Nb(5+).

The mixed metal oxide compound may be supported on a suitable support such as silica, silicon nitride, colloidal silica, alumina, titania or aluminium phosphate. The support may or may not be an alkali metal doped support. If the support is alkali metal doped, the alkali metal doping agent may be selected from one or more of caesium, potassium, sodium, or lithium, preferably, caesium or potassium, more preferably, caesium. Alternatively, the mixed oxide may itself be doped with any one or more of the above mentioned doping metals representing $M^3$, particularly those of group 1 above.

Preferably, when a separate support for the catalyst of the first or second aspect is used, the weight ratio of catalyst:support is in the range 10:1 to 1:50, more preferably, 1:1 to 1:20, most preferably, 2:3 to 1:10.

Advantageously, unsaturated ester selectivity is increased by doping cations having a low charge to radius ratio thus caesium was found to be more selective than lithium. Preferably, therefore, if used, the doping metal cation is caesium, rubidium and/or potassium, more preferably, rubidium and/or caesium, most preferably caesium.

Preferably, the carboxylic acid or ester reactant of the present invention is of formula $R^3$—$CH_2$—$COOR^4$ wherein $R^4$ is either hydrogen or an alkyl group and $R^3$ is either hydrogen, an alkyl or aryl group.

According to a further aspect of the present invention there is provided a production process for the manufacture of ethylenically unsaturated carboxylic acids or esters thereof, preferably, an α, β ethylenically unsaturated carboxylic acid or ester, comprising the steps of contacting an alkanoic acid or ester of the formula $R^3$—$CH_2$—$COOR^4$ with formaldehyde or a suitable source thereof, optionally in the presence of an alcohol, wherein $R^3$ and $R^4$ are each independently hydrogen or an alkyl group and $R^3$ may also be an aryl group, in the presence of a catalyst effective to catalyse the reaction, wherein the catalyst is in accordance with the second aspect of the present invention.

A suitable source of formaldehyde may be a compound of formula I

wherein $R^5$ and $R^6$ are independently selected from $C_1$-$C_{12}$ hydrocarbons or H, X is O, n is an integer from 1 to 100, and m is 1.

Preferably, $R^5$ and $R^6$ are independently selected from $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H. Preferably, n is an integer from 1 to 10, more preferably 1 to 5, especially, 1-3. However, other sources of formaldehyde may be used including trioxane.

Therefore, a suitable source of formaldehyde includes any equilibrium composition which may provide a source of formaldehyde. Examples of such include but are not restricted to methylal (1,1 dimethoxymethane), trioxane, polyoxymethylenes $R^1$—O—$(CH_2$—$O)_i$—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propionate.

Typically, the polyoxymethylenes are higher formals or hemiformals of formaldehyde and methanol $CH_3$—O—$(CH_2$—$O)_i$—$CH_3$ ("formal-i") or $CH_3$—O—$(CH_2$—$O)_i$—H ("hemiformal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—$(CH_2$—O—$)_iR^{32}$, where $R^{31}$ and $R^{32}$ may be the same or different groups and at least one is selected from a $C_2$-$C_{10}$ alkyl group, for instance $R^{31}$=isobutyl and $R^{32}$=methyl.

Preferably, the suitable source of formaldehyde is selected from methylal, higher hemiformals of formaldehyde and methanol, $CH_3$—O—$(CH_2$—$O)_i$—H where i=2, formalin or a mixture comprising formaldehyde, methanol and methyl propionate.

Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol:water in the ratio 30 to 60%; 0.03 to 20%:35 to 60% by weight. Most preferably, by the term formalin is meant a mixture of formaldehyde:methanol:water in the ratio 35 to 55%:0.05 to 18%: 42 to 53% by weight.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

Preferably, the ethylenically unsaturated acid or ester produced by the process of the invention is selected from methacrylic acid, acrylic acid, methyl methacrylate, ethyl acrylate or butyl acrylate, more preferably, it is an ethylenically unsaturated ester, most preferably, methyl methacrylate.

The process of the invention is particularly suitable for the production of acrylic, alkacrylic, 2-butenoic, cyclohexenoic, maleic, itaconic and fumaric acids and their alkyl esters. Suitable, alkacrylic acids and their esters are $(C_{0-8}alk)$acrylic acid or alkyl ($C_{0-8}$alk)acrylates, typically from the reaction of the corresponding alkanoic acid or ester thereof with a methylene source such as formaldehyde in the presence of the catalyst, preferably the production of methacrylic acid or especially methyl methacrylate (MMA) from propanoic acid or methyl propionate respectively.

The reaction of the present invention may be a batch or continuous reaction.

The term "alkyl" when used herein, means, unless otherwise specified, $C_1$ to $C_{12}$ alkyl and includes methyl, ethyl, ethenyl, propyl, propenyl butyl, butenyl, pentyl, pentenyl, hexyl, hexenyl and heptyl groups, preferably, methyl, ethyl, propyl, butyl, pentyl and hexyl. Unless otherwise specified, alkyl groups may, when there is a sufficient number of carbon atoms, be linear or branched, be cyclic, acyclic or part cyclic/acyclic, be unsubstituted, substituted or terminated by one or more substituents selected from halo, cyano, nitro, —$OR^{19}$, —$OC(O)R^{20}$, —$C(O)R^{21}$, —$C(O)OR^{22}$, —$NR^{23}R^{24}$, —$C(O)NR^{25}R^{26}$, —$SR^{29}$, —$C(O)SR^{30}$, —$C(S)NR^{27}R^{28}$, unsubstituted or substituted aryl, or unsubstituted or substituted Het, wherein $R^{19}$ to $R^{30}$ here and generally herein each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilicon groups, or mixtures thereof. Preferably, the alkyl groups are unsubstituted, preferably, linear and preferably, saturated.

The term "alkenyl" should be understood as "alkyl" above except at least one carbon carbon bond therein is unsaturated and accordingly the term relates to $C_2$ to $C_{12}$ alkenyl groups.

The term "alk" or the like should, in the absence of information to the contrary, be taken to be in accordance with the above definition of "alkyl" except "$C_0$ alk" means non-substituted with an alkyl.

The term "aryl" when used herein includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "halo" when used herein means a chloro, bromo, iodo or fluoro group, preferably, chloro or fluoro.

Without prejudice to the scope of protection and without being bound by theory, upon making this surprising discovery, the inventors tested whether there may be a diene impurity that was causing the colouration. However, reaction with the dienophile does not seem to affect the diene impurities identified, indicating that the impurity may not be a diene.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, $N(R^{23})R^{24}$, —$C(O)N(R^{25})R^{26}$, —$SR^{29}$, $C(O)SR^{30}$ or —$C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl, Substitution at Het may be at a carbon atom of the Het ring or, where appropriate, at one or more of the heteroatoms.

"Het" groups may also be in the form of an N oxide.

Suitable optional alcohols for use in the catalysed reaction of the present invention may be selected from a $C_1$-$C_{30}$ alkanol, including aryl alcohols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{27}R^{28}$, $SR^{29}$ or $C(O)SR^{30}$ as defined herein.

Highly preferred alkanols are $C_1$-$C_8$ alkanols such as methanol, ethanol, propanol, iso-propanol, iso-butanol, t-butyl alcohol, phenol, n-butanol and chlorocapryl alcohol. Although the monoalkanols are most preferred, poly-alkanols, preferably, selected from di-octa ols such as diols, trials, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol. The amount of alcohol is not critical. Generally, amounts are used in excess of the amount of substrate to be esterified. Thus the alcohol may serve as the reaction solvent as well, although, if desired, separate or further solvents may also be used.

Typical conditions of temperature and pressure in the process of the invention are between 100° C. and 400° C., more preferably, 200° C. and 375° C., most preferably, 300° C. and 360° C.; between 0.001 MPa and 1 MPa, more preferably, 0.03 MPa and 0.5 MPa, most preferably, between 0.03 MPa and 0.3 MPa.

Contact times for the reactants in the presence of the catalyst are dependent on temperature, pressure, the nature of any support and the concentration of the catalyst with respect to any support but are typically between 0.05 and 150 secs, more preferably, 0.1 and 120 secs, most preferably, 0.5 and 60 secs, especially, 1 and 20 secs.

The amount of catalyst used in the process of the present invention is not necessarily critical and will be determined by the practicalities of the process in which it is employed. However, the amount of catalyst will generally be chosen to effect the optimum selectivity and yield. Nevertheless, the skilled person will appreciate that the minimum amount of catalyst should be sufficient to bring about effective catalyst surface contact of the reactants during the contact time. In addition, the skilled person would appreciate that there would not really be an upper limit to the amount of catalyst relative to the reactants but that in practice this may be governed again by the contact time required.

The relative amount of reagents in the process of the invention can vary within wide limits but generally the mole ratio of formaldehyde or suitable source thereof to the carboxylic acid or ester is within the range of 20:1 to 1:20, more preferably, 5:1 to 1:15, The most preferred ratio will depend on the form of the formaldehyde and the ability of the catalyst to liberate formaldehyde from the formaldehydic species. Thus highly reactive formaldehydic substances where one or both of $R^{31}$ and $R^{32}$ in $R^{31}O-(CH_2-O-)_rR^{32}$ is H require relatively low ratios, typically, in this case, the mole ratio of formaldehyde or suitable source thereof to the carboxylic acid or ester is within the range of 1:1 to 1:9. Where neither of $R^{31}$ and $R^{32}$ is H, as for instance in $CH_3O-CH_2-OCH_3$, or in trioxane higher ratios are most preferred, typically, 3:1 to 1:3.

As mentioned above, due to the source of formaldehyde, water may also be present in the reaction mixture. Depending on the source of formaldehyde, it may be necessary to remove some or all of the water therefrom prior to catalysis. Maintaining lower levels of water than that in the source of formaldehyde may be advantageous to the catalytic efficiency and/or subsequent purification of the products. Water at less than 10 mole % in the reactor is preferred, more preferably, less than 5 mole %, most preferably, less than 2 mole %.

The molar ratio of alcohol to the acid or ester is typically within the range 20:1 to 1:20, preferably 10:1 to 1:10, most preferably 5:1 to 1:5, for example 1:1. However the most preferred ratio will depend on the amount of water fed to the catalyst in the reactants plus the amount produced by the reaction, so that the preferred molar ratio of the alcohol to the total water in the reaction will be at least 1:1 and more preferably at least 3:1.

The reagents may be fed to the reactor independently or after prior mixing and the process of reaction may be continuous or batch. Preferably, however, a continuous process is used.

Typically, the reaction takes place in the gas phase. Accordingly, suitable condensing equipment is generally required to condense the product stream after reaction has taken place. Similarly, a vaporiser may be used to bring the reactants up to temperature prior to the catalyst bed.

DETAILED DESCRIPTION

It is to be understood by a person having ordinary skill in the art that the present discussion is a description of exemplary embodiments only and is not intended as limiting the broader aspects of the present invention. The following example is provided to further illustrate the invention and is not to be construed to unduly limit the scope of the invention. Embodiments of the invention will now be described with reference to the following non-limiting examples and by way of illustration only.

EXPERIMENTAL

Example 1

10 g of aluminum chloride $AlCl_3$ in 15 ml of demineralised water with 0.1 ml of nitric acid $HNO_3$ were added dropwise to 22.4 g of antimony chloride $SbCl_5$ while stirring. In order to precipitate aluminium antimonate a solution of ammonium hydroxide was added until pH 7 was reached. The reaction mixture was aged for 1 hr, after that it was filtered and washed with a copious amount of water. It was dried at 80° C. overnight and then calcined in air at 600° C. for 1 hr.

Catalyst testing: 3 g of catalyst was placed in a stainless steel tubular reactor connected to a vaporiser. The reactor was heated to 350° C. and the vapouriser to 300° C. The mixture of 56.2 mole % of methyl propionate, 33.7 mole % of methanol, 9.6 mole % of formaldehyde and 0.5 mole % of water was passed through. The condensed reaction mixture was analysed by gas chromatography equipped with CP-Sil 1701.

Comparative Example 1

37.5 g of aluminum nitrate nonahydrate $Al(NO_3)_3 \cdot 9H_2O$ and 13.2 g of diammonium hydrogen phosphate $(NH_4)_2HPO_4$ were dissolved together in 160 ml of demineralised water acidified with nitric acid $HNO_3$. Solution of ammonium hydroxide was added until pH 7 was reached. Formed hydrogel was mixed for further 1 hr, after that it was filtered and washed with water. It was dried at 80° C. overnight and then calcined in air at 600° C. for 1 hr.

The catalyst was tested as described in example 1.

Example 2

17.3 g of titanium chloride $TiCl_5$ were added slowly to 54.5 g of antimony chloride $SbCl_5$ in 7 ml of demineralised water while mixing. Subsequently the solution was diluted with 160 ml of demineralised water. The precipitate was stirred for 6 hrs at 100° C., and then left to stand at room temperature overnight. Finally, it was filtered and washed with demineralised water, dried at 110° C. overnight and then calcined in air at 600° C. for 1 hr.

The catalyst was tested as described in example 1.

Comparative Example 2

7.9 g of diammonium hydrogen phosphate $(NH_4)_2HPO_4$ in 50 ml of demineralised water were added dropwise to 11.4 g titanium chloride $TiCl_5$ in 200 ml of demineralised water acidified with nitric acid $HNO_3$ and stirred for 3 hrs. It was filtered and washed with water. It was dried at 110° C. overnight and then calcined in air at 550° C. for 1 hr.

The catalyst was tested as described in example 1.

Example 3

5 g of gallium chloride $GaCl_3$ in 25 ml of demineralised water acidified with nitric acid $HNO_3$ were added dropwise to 8.6 g of antimony chloride $SbCl_5$ in 5 ml of demineralised water while stirring. Subsequently a solution of ammonium hydroxide was added until pH 7 was reached. The reaction mixture was aged for 1 hr, after that it was filtered and washed with a copious amount of water. It was dried at 80° C. overnight and then calcined in air at 600° C. for 1 hr.

The catalyst was tested as described in example 1.

Example 4

8.5 g of indium chloride $InCl_3$ in 25 ml of demineralised water acidified with nitric acid $HNO_3$ were added dropwise to 11.3 g of antimony chloride $SbCl_5$ in 5 ml of demineralised water while stirring. The mixture was diluted by addition of a further 25 ml of demineralised water. Subsequently a solution of ammonium hydroxide was added until pH 7 was reached. The reaction mixture was aged for 1 hr, after that it was filtered and washed with a copious amount of water. It was dried at 80° C. overnight and then calcined in air at 600° C. for 1 hr.

The catalyst was tested as described in example 1.

Example 5

10 g of aluminum chloride $AlCl_3$ in 20 ml of demineralised water acidified with nitric acid $HNO_3$ were mixed with 20.3 g of niobium chloride $NbCl_5$ in 30 ml of demineralised water acidified with nitric acid $HNO_3$ while stirring. After that a solution of ammonium hydroxide was added until pH 7 was reached. This was aged for 1 hr, and then it was filtered and washed with a copious amount of water. It was dried at 80° C. overnight and then calcined in air at 600° C. for 1 hr.

The catalyst was tested as described in example 1.

Example 6

10.1 g of niobium chloride $NbCl_5$ in 25 ml of demineralised water acidified with nitric acid $HNO_3$ were added to 12.1 g of zirconium oxychloride $ZrOCl_2.8H_2O$ in 25 ml of demineralised water acidified with nitric acid $HNO_3$ while stirring. After that a solution of ammonium hydroxide was added until pH 7 was reached. This was aged for 1 hr, and then it was filtered and washed with a copious amount of water. It was dried at 80° C. overnight and then calcined in air at 600° C. for 1 hr.

The catalyst was tested as described in example 1.

Comparative Example 3

7.9 g of diammonium hydrogen phosphate $(NH_4)_2HPO_4$ dissolved in 50 ml of demineralised water were added dropwise to 19.3 g of zirconium oxychloride $ZrOCl_2.8H_2O$ dissolved in 200 ml of demineralised water acidified with nitric acid $HNO_3$ and stirred for 2 hrs. It was filtered and washed with water. It was dried at 110° C. overnight and then calcined in air at 550° C. for 1 hr.

The catalyst was tested as described in example 1.

Example 7

10.1 g of niobium chloride $NbCl_5$ in 25 ml of demineralised water acidified with nitric acid $HNO_3$ were added to 6.6 g of gallium chloride $GaCl_3$ in 25 ml of demineralised water acidified with nitric acid $HNO_3$ while stirring. After that a solution of ammonium hydroxide was added until pH 7 was reached. This was aged for 1 hr, and then it was filtered and washed with a copious amount of water. It was dried at 80° C. overnight and then calcined in air at 600° C. for 1 hr.

The catalyst was tested as described in example 1.

Example 8

11.4 g of yttrium chloride $YCl_3$ in 25 ml of demineralised water acidified with nitric acid $HNO_3$ were added to 10.1 g of niobium chloride $NbCl_5$ in 25 ml of demineralised water acidified with nitric acid $HNO_3$ while stirring. After that a solution of ammonium hydroxide was added until pH 7 was reached. This was aged for 1 hr, and then it was filtered and washed with a copious amount of water. It was dried at 80° C. overnight and then calcined in air at 600° C. for 1 hr.

The catalyst was tested as described in example 1.

Example 9

12.2 g of lanthanum hydrate nitrate $La(NO_3)_3.xH_2O$ in 20 ml of demineralised water acidified with nitric acid $HNO_3$ were added to 10.1 g. of niobium chloride $NbCl_5$ in 20 ml of demineralised water acidified with nitric acid $HNO_3$ while stirring. After that a solution of ammonium hydroxide was added until pH 7 was reached. This was aged for 1 hr, and then it was filtered and washed with a copious amount of water. It was dried at 80° C. overnight and then calcined in air at 600° C. for 1 hr.

The catalyst was tested as described in example 1.

Example 10

5 g of aluminum chloride $AlCl_3$ in 25 ml of demineralised water acidified with nitric acid $HNO_3$ were added to 13.4 g of tantalum chloride $TaCl_5$ in 25 ml of demineralised water acidified with nitric acid $HNO_3$ to while stirring. After that a solution of ammonium hydroxide was added until pH 7 was reached. This was aged for 1 hr, and then it was filtered and washed with a copious amount of water. It was dried at 80° C. overnight and then calcined in air at 600° C. for 1 hr.

The catalyst was tested as described in example 1.

Example 11

6.1 g of lanthanum hydrate nitrate $La(NO_3)_3.xH_2O$ in 12.5 ml of demineralised water acidified with nitric acid $HNO_3$ were added to 6.7 g of tantalum chloride $TaCl_5$ in 12.5 ml of demineralised water acidified with nitric acid $HNO_3$ to while stirring. After that a solution of ammonium hydroxide was added until pH 7 was reached. This was aged for 1 hr, and then it was filtered and washed with a copious amount of water. It was dried at 80° C. overnight and then calcined in air at 600° C. for 1 hr.

The catalyst was tested as described in example 1.

Example 12

10 g of aluminum chloride $AlCl_3$ and 10.1 g of niobium chloride were mixed with 25 ml of demineralised water acidified with nitric acid $HNO_3$ each separately. Then the reactants were mixed together and added dropwise to 11.2 g of antimony chloride $SbCl_5$ in 5 ml of demineralised water while stirring. Subsequently solution of ammonium hydroxide was added until pH 7 was reached. The reaction mixture was aged for 1 hr, after that it was filtered and washed with a copious amount of water. It was dried at 80° C. overnight and then calcined in air at 600° C. for 1 hr.

The catalyst was tested as described in example 1.

Example 13

5 g of aluminum chloride $AlCl_3$ and 9.1 g of niobium chloride were mixed with 25 ml of demineralised water acidified with nitric acid $HNO_3$ each separately. Then the reactants were mixed together and added dropwise to 1.12 g of antimony chloride $SbCl_5$ in 1 ml of water while stirring. Subsequently solution of ammonium hydroxide was added until pH 7 was reached. The reaction mixture was aged for 1 hr, after that it was filtered and washed with copious amount of water. It was dried at 80° C. overnight and then calcined in air at 600° C. for 1 hr.

The catalyst was tested as described in example 1.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

TABLE 1

| | Catalyst | Contact time [s] | HCHO conversion [%] | MMA + MAA yield [%] | MAA selectivity [%] | MMA + MAA selectivity [%] | DME [mole %] | Toluene [mole %] | MMA + MAA yield [%]/ contact time [s] | DME [mole %]/ MMA + MAA yield |
|---|---|---|---|---|---|---|---|---|---|---|
| Ex 1 | AlSbO | 0.42 | 80.7 | 6.9 | 0.2 | 82.4 | 0.04 | 0.0003 | 16.43 | 0.006 |
| Comp Ex 1 | AlPO | 1.47 | 52.1 | 4.8 | 12.9 | 78.0 | 10.6 | 0.0045 | 3.26 | 2.2 |
| Ex 2 | TiSbO | 1.42 | 67.6 | 4.8 | 2.0 | 79.0 | 0.014 | 0.0001 | 3.38 | 0.003 |
| Comp Ex 2 | TiPO | 1.49 | 59.6 | 4.4 | 6.1 | 85.8 | 8.3 | 0.0004 | 2.95 | 1.9 |

TABLE 2

| | Catalyst | Contact time [s] | HCHO conversion [%] | MMA + MAA yield [%] | MAA selectivity [%] | MMA + MAA selectivity [%] | DME [mole %] | Toluene [mole %] | MMA + MAA yield [%]/ contact time [s] | DME [mole %]/ MMA + MAA yield |
|---|---|---|---|---|---|---|---|---|---|---|
| Ex 3 | GaSbO | 1.12 | 88.9 | 6.5 | 1.9 | 77.8 | 0.03 | 0.00004 | 5.80 | 0.005 |
| Ex 4 | InSbO | 0.37 | 85.1 | 3.5 | 1.5 | 69.7 | 0.003 | 0.00004 | 9.45 | 0.0009 |

TABLE 3

| | Catalyst | Contact time [s] | HCHO conversion [%] | MMA + MAA yield [%] | MAA selectivity [%] | MMA + MAA selectivity [%] | DME [mole %] | Toluene [mole %] | DEK selectivity [%] | MMA + MAA yield [%]/ contact time [s] | DME [mole %]/ MMA + MAA yield |
|---|---|---|---|---|---|---|---|---|---|---|---|
| Ex 5 | AlNbO | 2.97 | 71.7 | 5.9 | 2.7 | 85.1 | 1.4 | 0.0012 | 0.6 | 1.99 | 0.2 |
| Comp Ex 1 | AlPO | 1.47 | 52.1 | 4.8 | 12.9 | 78.0 | 10.6 | 0.0045 | 0.9 | 3.26 | 2.2 |
| Ex 6 | ZrNbO | 0.6 | 84.3 | 5.5 | 3.8 | 80.6 | 4.3 | 0.0020 | 0.4 | 9.16 | 0.8 |
| Comp Ex 3 | ZrPO | 0.41 | 89.1 | 4.0 | 7.5 | 64.6 | 9.3 | 0.0042 | 1.2 | 9.76 | 2.3 |

TABLE 4

| | Catalyst | Contact time [s] | HCHO conversion [%] | MMA + MAA yield [%] | MAA selectivity [%] | MMA + MAA selectivity [%] | DME [mole %] | Toluene [mole %] | DEK selectivity [%] | MMA + MAA yield [%]/ contact time [s] | DME [mole %]/ MMA + MAA yield |
|---|---|---|---|---|---|---|---|---|---|---|---|
| Ex 7 | GaNbO | 0.35 | 66.1 | 3.1 | 3.7 | 81.6 | 5.3 | 0.0014 | 0.6 | 8.97 | 1.7 |
| Ex 8 | YNbO | 0.51 | 62.8 | 2.9 | 3.0 | 70.6 | 3.0 | 0.0017 | 0.5 | 5.68 | 1.0 |
| Ex 9 | LaNbO | 2.13 | 42.8 | 2.2 | 2.4 | 84.2 | 0.4 | 0.0005 | 0.5 | 1.03 | 0.2 |

TABLE 5

| | Catalyst | Contact time [s] | HCHO conversion [%] | MMA + MAA yield [%] | MAA selectivity [%] | MMA + MAA selectivity [%] | DME [mole %] | Toluene [mole %] | MMA + MAA yield [%]/ contact time [s] | DME [mole %]/ MMA + MAA yield |
|---|---|---|---|---|---|---|---|---|---|---|
| Ex 10 | AlTaO | 2.68 | 69.6 | 3.2 | 3.7 | 81.1 | 4.4 | 0.0007 | 1.19 | 1.4 |
| Ex 11 | LaTaO | 1.73 | 86.4 | 4.5 | 1.6 | 75.8 | 0.4 | 0.0001 | 3.75 | 0.09 |

TABLE 6

| Catalyst | Contact time [s] | HCHO conversion [%] | MMA + MAA yield [%] | MAA selectivity [%] | MMA + MAA selectivity [%] | DME [mole %] | Toluene [mole %] | DEK selectivity [%] | MMA + MAA yield [%]/ contact time [s] | DME [mole %]/ MMA + MAA yield |
|---|---|---|---|---|---|---|---|---|---|---|
| Ex 12  $AlSb_{0.5}Nb_{0.5}O$ | 1.96 | 83.1 | 7.2 | 1.6 | 81.1 | 0.6 | 0.0003 | 0.6 | 3.67 | 0.08 |
| Ex 13  $AlSb_{0.1}Nb_{0.9}O$ | 0.53 | 72.4 | 6.0 | 3.8 | 82.9 | 4.6 | 0.0013 | 0.3 | 11.3 | 0.8 |

What is claimed is:

1. A catalyst for the reaction of a suitable source of formaldehyde with a carboxylic acid or ester to produce an ethylenically unsaturated carboxylic acid or ester, wherein the catalyst comprises a metal oxide having at least two metal cations, $M^1$ and $M^2$, wherein $M^1$ is at least one metal selected from group 3 or 4 in the $4^{th}$ to $6^{th}$ periods of the periodic table, group 13 in the $4^{th}$ to $5^{th}$ periods of the periodic table, or the remaining elements in the lanthanide series including scandium, yttrium, the lanthanide elements, titanium, zirconium, hafnium, gallium, and indium and $M^2$ is at least one metal selected from group 5 in the $5^{th}$ or $6^{th}$ periods of the periodic table or group 15 in the $4^{th}$ or $5^{th}$ periods of the periodic table including niobium, tantalum, arsenic, and antimony and optionally, $M^3$ or $M^4$, wherein $M^3$ is selected from groups 1 and 2 of the periodic table and $M^4$ is selected from group 14 of the periodic table, wherein the ratio $M^1:M^2$ is in the range of from 5:1 to 1:5, and wherein the metal oxide catalyst compound of the invention does not include other metal types above a level 0.1 mol % other than the types $M^1$, $M^2$, $M^3$, or $M^4$.

2. A catalyst according to claim 1, wherein $M^1$ are cations in the 3+ oxidation state.

3. A catalyst according to claim 1, wherein $M^2$ are cations in the +5 oxidation state.

4. A catalyst according to claim 1, wherein the combinations of metal oxides for use in the present invention may be selected from the group consisting of: Ti\Sb oxide; Ga\Sb oxide; In\Sb oxide; Zr\Nb oxide; Ga\Nb oxide; Y\Nb oxide; La\Nb oxide; and La\Ta oxide which oxides are either unsupported or supported on a suitable support comprising alumina, silica, silicon nitride, colloidal silica, titania or aluminium phosphate.

5. A catalyst according to claim 1, wherein further metals or cations of $M^3$ and/or $M^4$ are present in the mixed metal oxide.

6. A catalyst according to claim 1, wherein the formula for the metal oxide is $M^1_n M^2_m M^3_q M^4_r O_p$ wherein $M^1$ is a cation, and $M^2$ is a cation, n, m and p may be a positive integer or decimal number and q and r may be a positive integer or decimal number and wherein:

at least one of $M^3$ or $M^4$ is a metal or cation.

7. A catalyst according to claim 1, wherein a binder is used and forms up to 50 wt % of the catalyst.

8. A process in the presence of a catalyst according to claim 1 for the production of an ethylenically unsaturated carboxylic acid or ester comprising the step of reacting a suitable source of formaldehyde with a carboxylic acid or ester.

9. A process for the production of ethylenically unsaturated carboxylic acids or esters according to claim 8, wherein the carboxylic acid or ester reactant of the present invention is of formula $R^3$—$CH_2$—$COOR^4$ wherein $R^4$ is either hydrogen or an alkyl group and $R^3$ is either hydrogen, an alkyl or aryl group.

10. A process for the production of ethylenically unsaturated carboxylic acids or esters according to claim 8, wherein the ethylenically unsaturated acid or ester produced by the process is selected from the group consisting of: methacrylic acid, acrylic acid, methyl methacrylate, ethyl acrylate and butyl acrylate.

11. The catalyst according to claim 6, wherein $M^1$ is a 3+ cation and $M^2$ is a 5+ cation.

12. The process of claim 8 wherein the reaction is carried out in the presence of an alcohol.

13. The process of claim 10 wherein the ethylenically unsaturated acid or ester produced by the process is methyl methacrylate.

14. The catalyst according to claim 1, wherein the ethylenically unsaturated carboxylic acid or ester is selected from α, β ethylenically unsaturated carboxylic acids or esters.

15. The process of claim 8, wherein metals or cations $M^3$ and/or $M^4$ are present in the mixed metal oxide.

16. A catalyst for the reaction of a suitable source of formaldehyde with a carboxylic acid or ester to produce an ethylenically unsaturated carboxylic acid or ester, wherein the catalyst comprises a metal oxide having at least two metal cations, $M^1$ and $M^2$, wherein $M^1$ is at least one metal selected from group 3 or 4 in the $4^{th}$ to $6^{th}$ periods of the periodic table, group 13 in the $4^{th}$ to $5^{th}$ periods of the periodic table, or the remaining elements in the lanthanide series including scandium, yttrium, the lanthanide elements, titanium, zirconium, hafnium, gallium, and indium and $M^2$ is at least one metal selected from group 5 in the $5^{th}$ or $6^{th}$ periods of the periodic table or group 15 in the $4^{th}$ or $5^{th}$ periods of the periodic table including niobium, tantalum, arsenic, and antimony and at least one of $M^3$ or $M^4$, wherein $M^3$ is selected from groups 1 and 2 of the periodic table and $M^4$ is selected from group 14 of the periodic table, wherein the ratio $M^1:M^2$ is in the range of from 5:1 to 1:5, and wherein the metal oxide catalyst compound of the invention does not include other metal types above a level 0.1 mol % other than the types $M^1$, $M^2$, $M^3$, or $M^4$.

* * * * *